US00PP08035P

United States Patent [19]

Augustine et al.

[11] Patent Number: Plant 8,035

[45] Date of Patent: Nov. 17, 1992

[54] STRAWBERRY PLANT CALLED "GRACE"

[75] Inventors: Jimmy J. Augustine; Peggy P. Chang, both of Naples, Fla.

[73] Assignee: BHN, A Joint Venture, North Naples, Fla.

[21] Appl. No.: 624,417

[22] Filed: Dec. 7, 1990

[51] Int. Cl.[5] ..... A01H 5/00

[52] U.S. Cl. ..... Plt./48

[58] Field of Search ..... Plt./48, 49

[56] References Cited

U.S. PATENT DOCUMENTS

P.P. 4,487 11/1879 Bringhurst et al. ..... Plt. 49

P.P. 4,538 5/1980 Bringhurst et al. ..... Plt. 49

P.P. 5,262 7/1984 Voth et al. ..... Plt. 48

*Primary Examiner*—James R. Feyrer

*Attorney, Agent, or Firm*—James Albert Drobile; Lois A. Gianneschi

[57] ABSTRACT

A new and distinct short-day cultivar of strawberry designated as "Grace" which is characterized by its capability of earliness, high yield, and good flavor. The plant produces fruit that are medium conic in shape with a slightly pointed tip and which are bright red in color. This cultivar is adapted to growing in the major fruit production areas of Florida.

3 Drawing Sheets

DESCRIPTION

This invention relates to a new and distinctive short-day type strawberry cultivar designated as "Grace" which is the result of a cross of BHN accession number 8231 and the short-day type strawberry cultivar known as "Pajaro" (U.S. Plant Pat. No. 4,538) made in the winter of 1982-1983. The male parent, "Pajaro", possesses the distinguishing characteristics of superior shape and flavor, good firmness and size, and late fruit production. The female parent, BHN 8231, possesses the distinguishing characteristics of earliness and high yield. The novel cultivar, "Grace", resembles the male parent in possessing good flavor and size, and resembles the female parent by possessing the characteristics of earliness and high yield. "Grace" is intermediate between its parents with respect to the characteristics of shape and firmness. The differences between "Grace" and its antecedents have been maintained throughout successive generations by asexual reproduction.

"Grace" first fruited in 1984 at the BHN Research facility in Naples, Fla., where it was selected and designated as 8307-183. It was later tested as advanced selection "BHN 2". "Grace" has been propagated asexually by runners and meristem culture and was trialed in growers' fields in North Carolina, Canada, and other Florida locations. The plants have been tested at BHN Research facilities in Naples and Bonita Springs, Fla.

"Grace" is an early fruiting cultivar which has performed well in Florida, where tested, and is competitive with the important cultivars grown in that area. "Grace" fruits earlier than "Pajaro" and "Chandler" (U.S. Plant Pat. No. 5,262), the two widely grown short-day cultivars in Florida at this time. "Grace" is also as early or earlier than "Douglas" (U.S. Plant Pat. No. 4,487), a short-day cultivar of previous importance in Florida and yields from "Grace" are greater than "Pajaro", "Chandler" or "Douglas".

Figure 1:
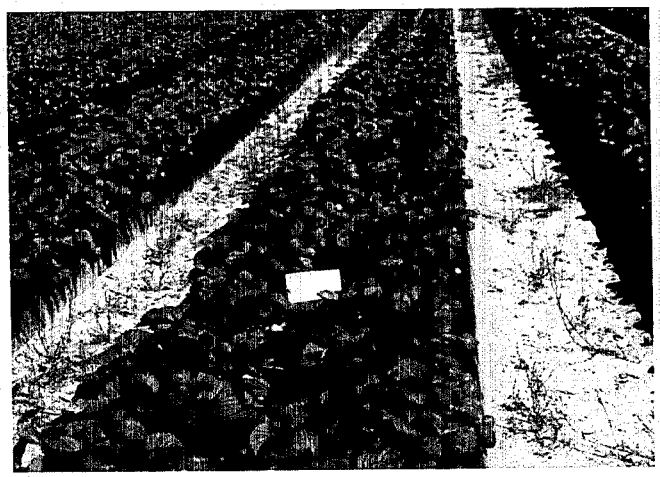
FIG. 1 shows typical growth of plants in a production field with plants in a stage of flowering and fruiting at about mid-season.
Figure 2:
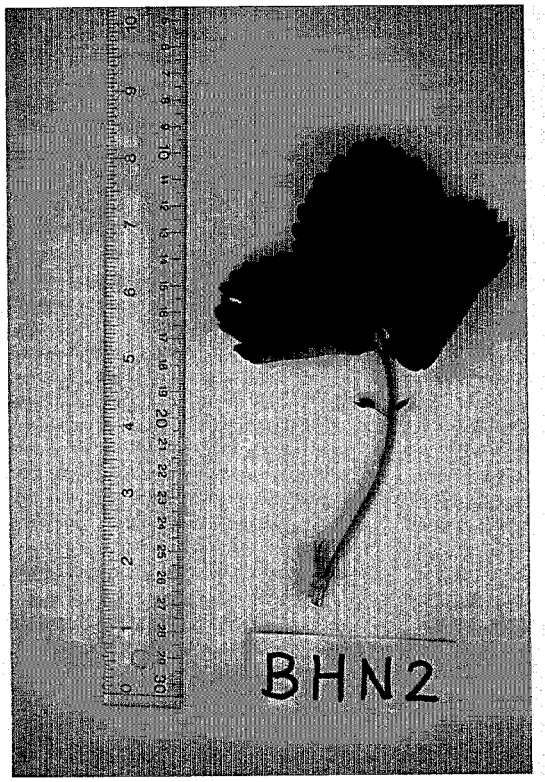
FIG. 2 depicts a typical mature compound leaf from a specimen of fruiting stage showing details of size, top and bottom coloration margin characteristics, leaf stem, and stipule characteristics.
Figure 4:
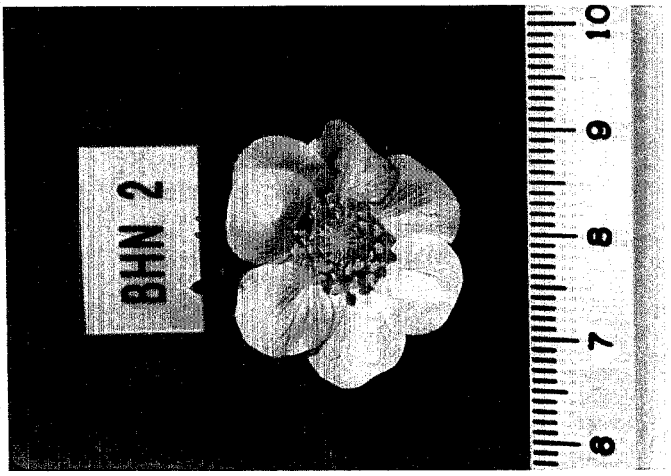
FIG. 4 shows a representative complete flower in late season and shows the relative size of calyx to petals; count, placement, attitude; coloration and margin characteristics of petals; and, the details and coloration of reproductive organs.
Figure 3:
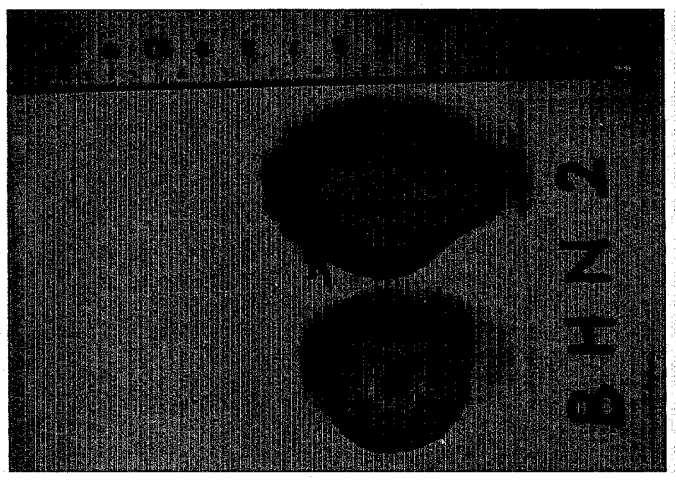
FIG. 3 illustrates cross and longitudinal sections of fruit, respectively, showing seed placement, flesh coloration, typical cavity shape and extent, and calyx character and attachment.
Figure 5:
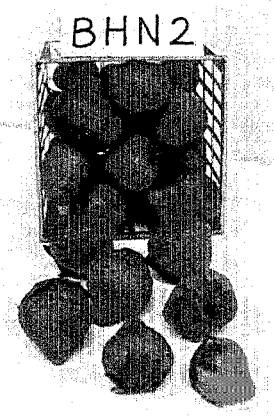
FIG. 5 shows plural fruit of the claimed plant reflecting the variation in fruit shape and size within market grade which may be produced by the claimed plant and shows seed and calyx placement relative to the fruit surface, as well as the attractive and uniform coloration of ripe fruit at harvest stage.

The distinctive characteristics of this new strawberry cultivar described in detail below were observed upon its discovery and throughout the repeated test periods.

Plants and Foliage

Leaf color and characteristics from late 1989 summer nursery plants of "Grace" are compared with those of "Pajaro", "Chandler" and "Douglas" in Table 1.

TABLE 1

| | Grace | Pajaro | Chandler | Douglas |
|---|---|---|---|---|
| Color | 7.5GY3/4 | 7.5GY3/6 | 5GY4/6 | 5GY5/8 |
| Shape (length/width) | 1.23 | 1.11 | 1.15 | 1.31 |
| Basal angle of terminal leaflet (degrees) | 71 | 75 | 76 | 58 |
| Size of terminal leaflets ($mm^2$) | 38 | 52 | 46 | 46 |
| Serrations of terminal leaflets | 12.2 | 14.6 | 14.0 | 13.8 |
| Petiolule length (mm) | 2.9 | 3.0 | 2.2 | 2.6 |
| Petiole length (mm)[1] | 147 | 152 | 182 | 187 |
| Bract leaflet | 81 | 77 | 74 | 72 |

TABLE 1-continued

| | Grace | Pajaro | Chandler | Douglas |
|---|---|---|---|---|
| position | | | | |

[1]Petiole data collected during the Spring 1990.

As shown above in Table 1, the leaf color of "Grace" is similar to that of "Pajaro" and is also less yellow than those of "Chandler" and "Douglas" (Munsell Color System). Terminal leaflets are somewhat elongate and similar to those of "Douglas" and less round than those of "Pajaro" and "Chandler" as shown by the length/-width measurements and half-blade terminal leaflet basal angles. "Grace" terminal leaflets are smaller than "Chandler", "Douglas", and "Pajaro" as determined by extracting the square root of the length times the width measurements. Terminal leaflet serration numbers are slightly less than those of "Pajaro", "Chandler", and "Douglas". Petiolules (terminal leaflet stems) are similar in length to those of "Pajaro" and slightly longer than those of "Chandler" and "Douglas". "Grace" plants are about the same size as that of "Pajaro", but smaller than those of "Chandler" and "Douglas", as indicated by petiole length. Bract leaflets occur on some of the petioles of "Grace" and are positioned slightly farther up the petioles (expressed as percent length of petiole) as those of "Pajaro", "Chandler", and "Douglas". The frequency of bracts on "Grace" (29%) is similar to that of "Chandler (20%) and "Douglas" (27%) and higher than "Pajaro" (6%). Runner production is excellent, being equal to or better than that of "Chandler" and "Douglas", and much better than that of "Pajaro".

Isozymes in Leaf Extracts

"Grace" has been classified for three enzyme systmes by starch gel electrophoresis: (A) phosphoglucose isomerase (PGI); (B) leucine amino peptidase (LAP); and (C) malate dehydrogenase (MDH). The isozyme patterns of "Grace", as they compare to other important Florida grown cultivars, are shown below in Table 2.

TABLE 2

| | Isozymes in Leaf Extracts by Electrophoresis | | | |
|---|---|---|---|---|
| | Grace | Pajaro | Chandler | Douglas |
| PGI | A4 | A4 | A1 | A3 |
| LAP | B3 | B3 | B3 | B3 |
| MDH | C1 | C2 | C2 | C2 |

"Grace" can be unambiguously distinguished from the three comparison cultivars ("Pajaro", "Chandler" and "Douglas") by using the isozyme patterns for MDH. (For the PGI and LAP procedures see: *J. Amer. Soc. Hort. Sci.* 106(5):684–687, (1981), which is incorporated herein by reference. For the MDH procedure see: USDA Forest Service General Technical Report PSW-64, (1982); and Tanksley, S. D. and Orton, T. J. *Isozymes in Plant Genetics and Breeding,* Part A, pp. 469–516 (Elsevier Science Publishers B.V., 1984.), which are also incorporated herein by reference.

Disease and Pest Reaction

"Grace" is slightly tolerant to anthracnose when compared to "Pajaro", "Chandler", and "Douglas". "Grace" is susceptible to the two-spotted mite, as are "Chandler" and "Douglas" and is less tolerant than "Pajaro".

Flowering, Fruiting, and Production Characteristics

"Grace" is an obligate short-day cultivar. As is typical of the species, the flowers are perfect; petals are pure white and have no margins; and anthers and receptacle are bright yellow. The distinguishing flower characteristics of "Grace" and the comparison cultivars are presented in Table 3. "Grace" has a higher petal, sepal, and anther number than all three check cultivars. "Grace" petals are smaller than those of "Pajaro", "Chandler", and "Douglas". Both "Grace" and "Pajaro" have conic-shaped receptacles, whereas "Chandler" and "Douglas" have wedge-shaped receptacles. These differences are reflected later in fruit shapes. The flowers are self-fertile and pollination is very good. Canadian-produced plants of "Grace" begin flowering about two weeks after planting and fruit typically begin to mature about six weeks after planting. The fruit shape is medium conic with a slightly pointed tip and under adverse weather conditions some fruit may be misshapen. Centers of the fruit are almost solid, showing little hollowing. The yield, fruit and quality characteristics of "Grace" are compared below with those of "Pajaro", "Chandler", and "Douglas" in Table 3.

TABLE 3

| | Grace | Pajaro | Chandler | Douglas |
|---|---|---|---|---|
| Petal Number | 7.2 | 5.0 | 5.9 | 5.8 |
| Sepal Number | 14.4 | 10.0 | 11.8 | 11.5 |
| Anther Number | 33.0 | 27.5 | 25.1 | 25.1 |
| Petal Breadth (cm) | 1.0 | 1.2 | 1.3 | 1.2 |
| Petal Axis Length (cm) | 1.0 | 1.2 | 1.2 | 1.2 |
| Receptacle Shape | conic | conic | wedge | wedge |

TABLE 4

| | Grace | Pajaro | Chandler | Douglas |
|---|---|---|---|---|
| Planting Date | 10-23 | 10-23 | 10-23 | 10-23 |
| First Harvest Date | 12-8 | 12-15 | 12-17 | 12-8 |
| First Harvest Peak | 12-28 | 1-5 | 1-5 | 1-5 |
| Second Harvest Peak | 2-21 | 3-15 | 3-15 | 3-15 |
| Last Harvest Date | 3-15 | 3-15 | 3-15 | 3-15 |
| Early Yield (g/plant) | 48 | 14 | 20 | 38 |
| Yield (g/plant) | 540 | 233 | 405 | 337 |
| Average Fruit Weight (g/fruit) | 15.6 | 14.3 | 17.1 | 17.5 |
| Primary Fruit Weight (g/fruit) | 25.0 | 21.6 | 17.1 | 29.1 |
| Primary Fruit Breadth (cm) | 4.1 | 3.4 | 3.2 | 4.4 |
| Primary Fruit Axis Length (cm) | 4.8 | 4.3 | 4.1 | 4.7 |
| Secondary Fruit Weight (g/fruit) | 8.5 | 9.8 | 11.9 | 6.1 |
| Secondary Fruit Breadth (cm) | 2.4 | 2.7 | 2.9 | 2.2 |
| Secondary Fruit Axis Lenght (cm) | 3.1 | 2.9 | 3.4 | 2.9 |
| Firmness (g) | 208 | 250 | 258 | 186 |
| Color | 7.5R4/14 | 7.5R4/14 | 7.5R4/14 | 6.25R3/12 |
| Ascorbic Acid (mg/100 g) | 15.6 | 29.0 | 10.3 | 24.9 |
| Soluble Solids (degree brix) | 7.3 | 6.8 | 6.9 | 7.4 |

The yield and average fruit weight data in Table 4 were collected and averaged from plants produced from meristem culture, runner plants produced in North Carolina and Canada, and trailed with three growers in the Plant City area of Florida during the winter of 1988–1989. Data on primary and secondary fruit in Table 4 were collected from plants produced from meristem culture, runner plants produced in Canada, and the fruiting nursery at the BHN Research Facility in Bonita Springs, Fla. during the winter of 1991–1992. The fruit quality data were collected from plants produced from meristem culture, runner plants produced in North Carolina and Canada and the fruiting nursery at the BHN Research Facility in Bonita Springs Fla. during the winter of 1988–1989.

Harvesting from "Grace" starts as early as "Douglas" and is earlier than "Pajaro" and "Chandler" by one or two weeks. First harvest peak of "Grace" is substantially earlier than that of the comparison cultivars. "Grace" is competitive with "Douglas" in producing early yield and superior to "Pajaro" and "Chandler". Second harvest peak of "Grace" is also much earlier than the other three cultivars, and "Grace" is superior to all three check cultivars for total yield. Average fruit weight of "Grace" is about the same as that of "Pajaro", but somewhat smaller than "Chandler" and "Douglas". Primary fruit weight and size of "Grace" is less than that of "Douglas" but higher than that of "Pajaro" and "Chandler". Secondary fruit of "Grace" are smaller than those of "Pajaro" and "Chandler", but slightly larger than those of "Douglas."

The fruit of "Grace" are firmer than those of "Douglas", but not as firm as "Pajaro" and "Chandler" as measured by an EFFEGI Fruit Pressure Tester equipped with a 5 mm diameter plunger tip. The fruit skin color of "Grace" is similar to those of "Pajaro" and "Chandler", but not as dark as that of "Douglas" (Munsell Color System). The finish is glossy and attractive. The flesh color is about the same as the skin and only slightly less intense with a smaller amount of white tissue around the core. The achenes are medium sized (smaller than those of "Douglas"), yellow, and positioned slightly above the skin surface. The calyx is medium sized and positioned even with the base of the fruit. The fruit of "Grace" are highly resistant to cracking after rain similar to "Chandler" and more crack resistant than "Pajaro" and "Douglas". The ascorbic acid content is higher than that of "Chandler", but less than that of "Pajaro" and "Douglas" as measured by the tetrametric method (AOAC method 43064, 14th ed). The soluble solids content is similar to that of the three comparative cultivars. The flavor of "Grace" is very good and moderate subacid, being about as sharp as "Chandler". The fruit is recommended for fresh market and is competitive in Florida because of its earliness, high yield, and excellent fruit quality.

We claim:

1. A new and distinct variety of strawberry plant named Grace, as herein described and illustrated.

* * * * *